United States Patent [19]

Srivastava

[11] Patent Number: 5,500,123
[45] Date of Patent: Mar. 19, 1996

[54] TWO-PHASE ANAEROBIC DIGESTION OF CARBONACEOUS ORGANIC MATERIALS

[75] Inventor: Vipul J. Srivastava, Woodridge, Ill.

[73] Assignee: Institute of Gas Technology, DesPlaines, Ill.

[21] Appl. No.: 336,332

[22] Filed: Nov. 8, 1994

Related U.S. Application Data

[63] Continuation of Ser. No. 174,958, Dec. 28, 1993, abandoned.

[51] Int. Cl.$^6$ ..................................................... C02F 3/28
[52] U.S. Cl. ........................... 210/603; 210/613; 210/622; 210/630
[58] Field of Search ..................................... 210/603, 605, 210/607, 609, 613, 620, 622, 630, 631, 912

[56] References Cited

U.S. PATENT DOCUMENTS

| | | | |
|---|---|---|---|
| 4,022,665 | 5/1977 | Ghosh et al. | 195/27 |
| 4,318,993 | 3/1982 | Ghosh et al. | 210/603 |
| 4,323,367 | 4/1982 | Ghosh | 210/603 |
| 4,358,537 | 11/1982 | Chynoweth | 435/162 |
| 4,366,059 | 12/1982 | Witt | 210/631 |
| 4,396,402 | 8/1983 | Ghosh | 210/603 |
| 4,568,457 | 2/1986 | Sullivan | 210/603 |
| 4,636,467 | 1/1987 | Chynoweth | 435/140 |
| 4,696,746 | 9/1987 | Ghosh et al. | 210/603 |
| 4,722,741 | 2/1988 | Hayes et al. | 210/603 |
| 4,735,724 | 4/1988 | Chynoweth et al. | 210/603 |
| 4,826,600 | 5/1989 | Ely et al. | 210/603 |
| 5,228,995 | 7/1993 | Stover | 210/603 |

FOREIGN PATENT DOCUMENTS

| | | |
|---|---|---|
| 0097388 | 1/1984 | European Pat. Off. . |
| 0566056 | 10/1993 | European Pat. Off. . |
| 401052 | 8/1924 | Germany . |

OTHER PUBLICATIONS

Chynoweth, D. P. et al., "Biological Assessments of Anaerobic Digestion of Municipal Solid Waste", final report submitted to the Solar Energy Research Institute under U.S. DOE Contract No. DE–AC02–83CH10093, May 1991.

Srivastava, Vipul J. et al., "Methane Enrichment Digestion Experiments at the Anaerobic Experimental Test Unit at Walt Disney World", Final Report, Jun. 1993.

Chynoweth, David P. et al., "Microbial Production of Road Salt (Calcium Magnesium Acetate) From Biomass", A Proposal submitted to Minnesota Gas Company, Sep. 1983.

Pohland, F. G. et al., "Developments in Anaerobic Treatment Processes", *Bio–Technology and Bio–Engineering*, Symposium No. 2,85–106, John Wiley & Sons, Inc., 1971.

Pohland, F. G. et al., "Developments in Anaerobic Stabilization of Organic Wastes—The Two–Phase Concept", *Environmental Letters*, 1(4), pp. 255–266, Marcel Dekker, Inc., 1971.

Primary Examiner—Thomas Wyse
Attorney, Agent, or Firm—Speckman, Pauley & Fejer

[57] ABSTRACT

A process for improved methane production by two-phase anaerobic digestion of organic carbonaceous material in which organic carbonaceous material is fermented under anaerobic conditions in an acid phase digester, forming a liquid/solids effluent, the liquid/solids effluent is fermented under anaerobic conditions in a methane phase digester, product gas comprising methane is withdrawn from the methane phase digester, and oxygen is introduced into the methane phase digester. In a preferred embodiment, the methane phase liquid effluent is passed through a $CO_2$ stripper resulting in stripping of $CO_2$ and $H_2S$ from the methane phase liquid effluent. The resulting stripper liquid effluent comprising dissolved oxygen is then recycled back to the methane phase digester.

13 Claims, 1 Drawing Sheet

TWO-PHASE ANAEROBIC DIGESTION OF CARBONACEOUS ORGANIC MATERIALS

This application is a continuation of application No. 08/174,958, filed Dec. 28, 1993, abandoned.

BACKGROUND OF THE INVENTION

1. Field of the Invention

This invention relates to a process for improved methane production by two-phase anaerobic digestion of organic carbonaceous materials. More particularly, this invention relates to an improved two-phase anaerobic digestion process for methane production wherein conditions are provided to efficiently conduct an acid forming phase and to separately conduct a methane production phase. More particularly, this invention relates to an anaerobic digestion process for producing methane from a wide variety of biomass and/or solid organic wastes.

2. Description of Prior Art

Anaerobic digestion is known for stabilizing sludge and predominately organic materials and for producing usable product gas of varying composition. The organic feed mixture that provides the substrate for anaerobic biodegradation may comprise a wide variety of organic carbon sources, ranging from raw sewage, sludge to municipal refuse, or biomass material such as plants and crop waste. The process of anaerobic digestion biodegrades any of these organic carbonaceous materials, under appropriate operating conditions, to form product gas that contains desirable methane gas. A typical anaerobic digester product gas may contain, on a dry basis, 55% to 65% methane, 35% to 45% carbon dioxide, and less than 1% of other gases.

Current practice of digesting solid organic wastes in landfills is inefficient while anaerobic digestion of solid organic wastes in a tank-based system requires extensive front-end processing and careful classification of the waste to be processed. In addition, upgrading the gas mixture to a pipeline quality gas, that is, a gas having greater than 95% methane, using known unit processes for carbon dioxide, hydrogen sulfide, and moisture removal, are expensive and may exceed the digestion costs.

Separated two-phase anaerobic digestion processes, where the acid phase digestion and the methane phase digestion are carried out in two separate reactor vessels, have been found to enhance the efficiency of conversion of organic carbonaceous materials to methane, such as described in Pohland and Ghosh, *Bio-Technology and Bio-Engineering* Symposium No. 2, 85-106 (1971) John Wiley and Sons, Inc., and by the same authors in *Environmental Letters*, 1(4), 255–266 (1971), Marcel Dekker, Inc. In an acid first phase, the microbial population and operating conditions are selected to promote the conversion of organic carbonaceous matter to volatile fatty acids of low molecular weight. The volatile fatty acids remain solubilized in the liquid portion of the digester contents. The liquid/solid effluent from the acid first phase is conveyed to a methane second phase, in which methanogenic microorganisms convert the volatile fatty acids to product gas composed primarily of methane and carbon dioxide. Product gas is removed from the methane second phase and processed or scrubbed to separate the methane component that is drawn off as pipeline gas. As previously stated, the gas separation of methane is an expensive process that detracts from the economic feasibility of the anaerobic biodegradation of organic carbonaceous material to produce methane gas.

Two-phase anaerobic digestion of organic carbonaceous materials to produce methane is generally taught by U.S. Pat. No. 4,022,665, U.S. Pat. No. 4,318,993, and U.S. Pat. No. 4,696,746. Each of these patents teaches the conduct of acid phase digestion and methane phase digestion in two separate reactor vessels. Each of these patents also teaches operating conditions for acid phase and methane phase digestion. The improved process of the present invention employs the operating conditions for a two-phase anaerobic digestion process, such as feed rates and detention times, taught by these patents and, thus, the teachings of these patents with respect to such operating conditions are incorporated herein by reference.

Two-phase anaerobic digestion can be carried out in a single digestion vessel as taught, for example, by U.S. Pat. No. 4,735,724 which teaches a non-mixed vertical tower anaerobic digester and anaerobic digestion process which provides passive concentration of biodegradable feed solids and microorganisms in an upper portion of a continuous digester volume and effluent withdrawal from the middle to the bottom portion of the digester, resulting in increased solids retention times, reduced hydraulic retention times, and enhanced bio-conversion efficiency.

To enhance the methane content of product gas derived from two-phase anaerobic digestion of organic carbonaceous materials, U.S. Pat. No. 4,722,741 teaches the removal of a large portion of carbon dioxide contaminate from the acid forming phase and from the liquid product of the acid forming phase, and by absorption of carbon dioxide into the liquid phase during the methane forming phase of the anaerobic digestion process. Chynoweth, D. P. et al., "Biological Assessments of Anaerobic Digestion of Municipal Solid Waste", final report submitted to the Solar Energy Research Institute under U.S. DOE Contract No. DE-AC02-83CH10093 teaches the use of air stripping of recirculated digester supernatant to enrich methane content of biogas produced in a combined acid phase/methane phase digester. This report also teaches that as the stripper aeration rate is gradually increased, the level of digester product gas methane concentration increases. The report further indicates that a biological impact assessment of the disclosed process indicates that the addition of air to the anaerobic digestion process does not have a negative impact on the digestion process, and, in fact, stimulates the ability of the overall digester microbial population to form methane. However, aeration of digester supernatant, for removal of carbon dioxide, was anticipated to have a potential influence on microbial activity within the digester system, resulting from shock to anaerobic bacteria during the aeration step, or to transport of oxygen back to the digester during supernatant recycle. Thus, in order to prevent the latter, aerated supernatant was retained in a holding tank to allow facultative bacteria to reduce dissolved oxygen levels. Accordingly, this report suggests that the presence of oxygen in a combined two phase-anaerobic digestion vessel may have negative impact with respect to the production of methane. Indeed, it is known that exposure of methanogenic microorganisms to oxygen kills the microorganisms.

SUMMARY OF THE INVENTION

It is an object of this invention to provide an anaerobic digestion process which can produce near pipeline quality gas, that is, gas having a methane content in excess of 80%.

It is another object of this invention to provide a process for improved methane production by two-phase anaerobic digestion which can digest a wide variety of organic carbonaceous materials including biomass and/or solid organic waste in a cost-effective manner and at higher efficiencies than known anaerobic digestion processes.

It is still another object of this invention to obtain higher efficiencies in anaerobic digestion of organic carbonaceous material by separating the acid forming phase from the methane forming phase so that each phase can be operated more efficiently to obtain greater advantages in the overall anaerobic digestive process for producing methane gas.

These and other objects of this invention are achieved by a process for improved methane production by two-phase anaerobic digestion of organic carbonaceous material in which the organic carbonaceous material is introduced into an acid phase digester and fermented therein, under anaerobic condition to form a liquid/solids effluent. As used throughout the specifications and claims, the term "organic carbonaceous material" means any organic carbon material including sewage sludge, solids refuse, food waste, biomass including plants, crops, plant and crop wastes and the like, and industrial liquid and solids wastes. It will also be apparent to those skilled in the art that "organic carbonaceous material" may also comprise metal compounds. The liquid/solids effluent from the acid phase digester is passed to a methane phase digester in which the liquid/solids effluent is fermented under anaerobic conditions producing a product gas comprising methane and a methane phase liquid effluent. The methane containing product gas is withdrawn from the methane phase digester and collected. The methane phase liquid effluent is passed to a $CO_2$ stripper in which carbon dioxide ($CO_2$) and hydrogen sulfide ($H_2S$) are stripped from the methane phase liquid effluent with air. The resulting stripper liquid effluent comprising dissolved oxygen is introduced into the methane phase digester, thereby providing a small amount of oxygen.

A critical feature of this invention is the addition of oxygen to the methane phase digester. Because methane phase digestion in accordance with this process is an anaerobic process, that is, a process in with methanogenic microorganisms, in the absence of oxygen, convert the volatile fatty acids in the liquid/solids effluent from the acid phase digester to product gas comprising primarily methane and carbon dioxide, it is, indeed, a surprising result that the addition of a small amount of oxygen in accordance with this invention increases the production of methane in the methane phase digester. This is even more surprising because it is known that methanogenic microorganisms die off in the presence of oxygen. Nevertheless, as a result of the addition of a small amount of oxygen to the methane phase digester, we are able to produce a product gas comprising in excess of 80% methane compared to product gases comprising 45% to 65% methane produced by known two-phase anaerobic digestion processes.

A second critical feature of the process of this invention is the requirement that the acid phase and methane phase digestion steps are carried out in separate reactor vessels as compared to two-phase anaerobic digestion processes carried out in combined acid phase/methane phase digestion reactors. The acid phase digestion system is known to contain facultative bacteria, some hydrolytic and acidogenic bacteria, which are known to utilize oxygen and produce more $CO_2$ and less methane. By conducting the acid phase digestion and methane phase digestion in separate reactor vessels in accordance with the process of this invention, the influence of facultative bacteria is minimized, thereby ensuring the availability of oxygen in the methane phase digester for promotion of methane production.

Although oxygen is introduced into the methane phase digester in accordance with one embodiment of this invention as dissolved oxygen in the liquid effluent from the $CO_2$ stripper, it is within the scope of this invention that other means for introducing oxygen into the methane phase digester are also suitable.

BRIEF DESCRIPTION OF THE DRAWINGS

The above-mentioned and other features and objects of this invention will be better understood from the following detailed description taken in conjunction with the drawings wherein.

DESCRIPTION OF PREFERRED EMBODIMENTS

Figure 1:
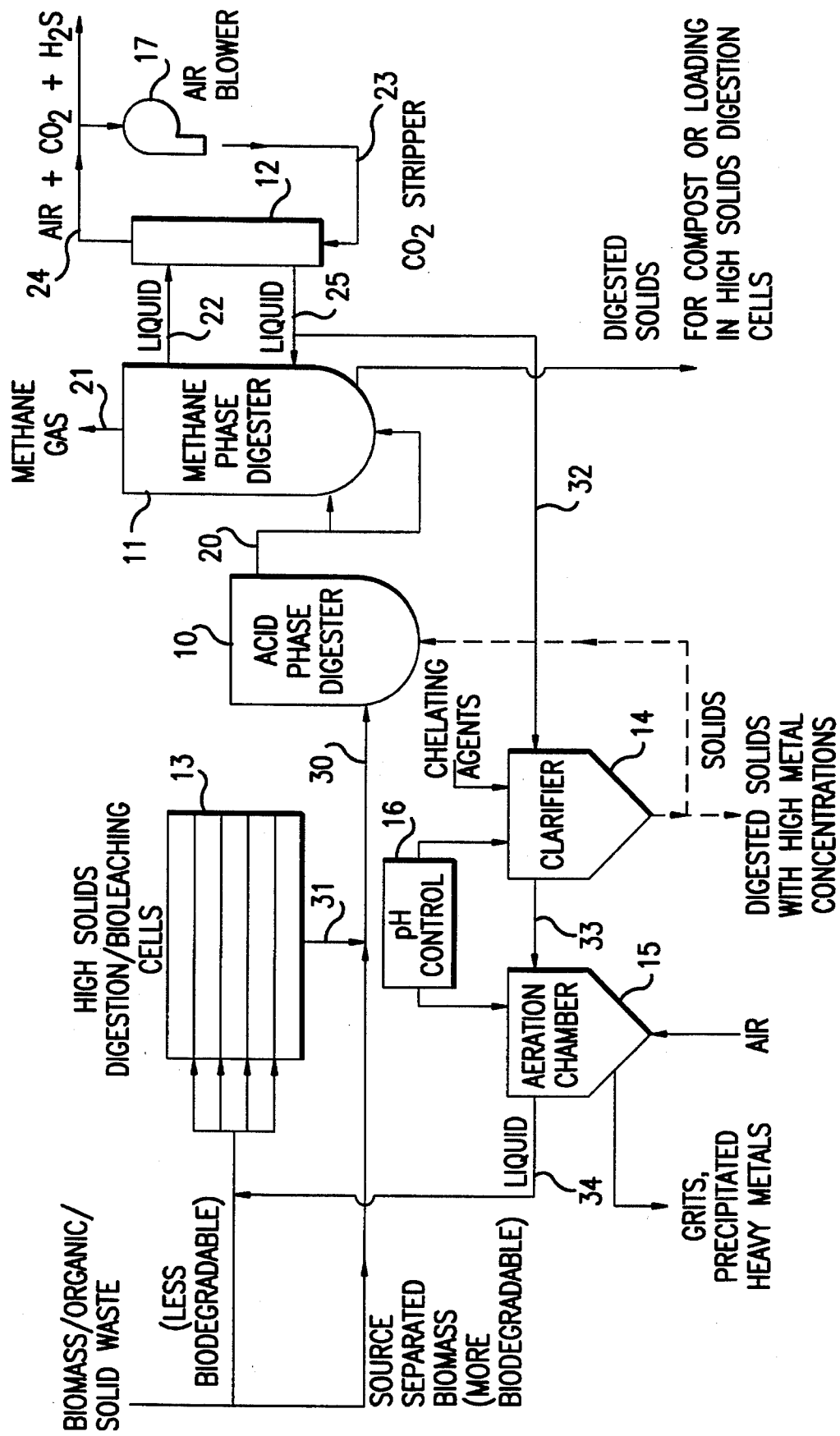
FIG. 1 is a schematic flow diagram of the two-phase anaerobic digestion process in accordance with one embodiment of this invention.

FIG. 1 shows a schematic diagram of a process for improved methane production by two-phase anaerobic digestion of organic carbonaceous material in accordance with one embodiment of this invention. As shown, organic carbonaceous material, preferably in the form of biomass/organic/solid waste is introduced into acid phase digester 10. The organic carbonaceous material is fermented in acid phase digester 10 under anaerobic conditions, forming a liquid/solids effluent. The liquid/solids effluent is passed through process line 20 from acid phase digester 10 directly into methane phase digester 11. The liquid/solids effluent from the acid phase digester is fermented in methane phase digester 11, also under anaerobic conditions, producing a methane phase liquid/solids effluent and a product gas comprising methane. The product gas comprising methane is withdrawn through process line 21 while the liquid portion of the methane phase liquid/solids effluent from methane phase digester 11 is passed through process line 22 into $CO_2$ stripper 12. The solids portion of the methane phase liquid/solids effluent is removed separately from methane phase digester 11. $CO_2$ stripper 12 is of a conventional type in which air from air blower 17 is introduced through process line 23 into $CO_2$ stripper 12 resulting in the desorption and removal through process line 24 of $CO_2$ and $H_2S$ dissolved in the methane phase liquid effluent. As a result of the stripping process, a small amount of oxygen is absorbed into the methane liquid effluent, forming a stripper liquid effluent which is subsequently passed through process line 25 from $CO_2$ stripper 12 into methane phase digester 11. In accordance with a particularly preferred embodiment of this invention, the amount of dissolved oxygen introduced into methane phase digester 11 comprises between about 2 mg/l (milligrams/liter) and about 50 mg/l of methane phase digester volume—day. Operation of the process above an oxygen level of about 50 mg/l of methane phase digester volume—day results in the destruction of some of the methanogenic microorganisms, while operation below about 2 mg/l of methane phase digester volume—day has no significant effect on the amount of methane produced.

To promote the separation of liquid and solid acid phase digester effluent within methane phase digester 11 where the organic carbonaceous material being digested comprises suspended solids, methane phase digester 11 is preferably a non-mechanically mixed reactor. Where the organic carbonaceous material comprises only liquids such as municipal sludge, any methane phase digester design will may be utilized.

In accordance with another preferred embodiment of this invention, to promote the efficient two-phase anaerobic digestion of the organic carbonaceous material, the organic carbonaceous material to be digested is separated, based on the biodegradability thereof, into a more biodegradable portion which can be introduced directly through process line 30 into acid phase digester 10 and a less biodegradable portion which is first hydrolyzed in bioleaching reactor 13. The leachate and any hydrolyzed solids formed in bioleaching reactor 13 are passed from bioleaching reactor 13 through process line 31 into process line 30 through which they are introduced into acid phase digester 10. Because only rapidly degradable organic carbonaceous materials are introduced into acid phase digester 10 in accordance with this embodiment of the invention, higher efficiency over conventional single stage digestion or regular two-phase digestion is obtained. In addition, capital costs are reduced because less expensive bioleaching cells, instead of expensive digesters, are employed for the rate limiting step of hydrolysis of less biodegradable organic carbonaceous material.

In accordance with another preferred embodiment of this invention, a portion of the stripper liquid effluent is processed to remove heavy metals present therein, thereby preventing metal toxicity to the digestion system as well as preventing the build up of heavy metals in the digested solids, the presence of which would adversely affect the market potential of the digested solids as a compost material. In particular, a portion of the stripper liquid effluent is passed through process line 32 into clarifier 14 resulting in separation of digested solids with high metal concentrations from the stripper liquid effluent. The clarified stripper liquid effluent, in accordance with another embodiment of this invention, is passed through process line 33 into aeration chamber 15 resulting in the reduction of any methanogenic population within the clarified stripper liquid effluent and removing grits and precipitated heavy metals therefrom. The aerated clarified stripper liquid effluent may then be pumped directly into acid phase digester 10 or alternatively into bioleaching reactor 13. Because the presence of methanogenic microorganisms in acid phase digester 10 inhibits the production of acids by the acidogenic microorganisms therein, it is important that aeration of the stripper liquid effluent be sufficient to prevent growth of methanogenic microorganisms in the stripper liquid effluent. To maintain the pH of the liquids within clarifier 14 and aeration chamber 15 at desired levels and to promote the precipitation of heavy metals therein as discussed hereinbelow, acid addition or caustic addition as required are provided by pH control means 16 to clarifier 14 and aeration chamber 15. The pH of the clarified and aerated liquid stream flowing from aeration chamber 15 through process line 34 into bioleaching reactor 13 is preferably in the range of about 5 to about 8, and more preferably in the range of about 5 to about 7.

In accordance with another embodiment of this invention, depending upon the chemistry of the stripper liquid effluent, metals associated with solids therein may be solubilized by adding chelating agents to clarifier 14 or by reducing the pH thereof to a range of about 3 to about 4. Metals may also be solubilized during anaerobic digestion, first in the acid phase digester where the pH of the liquids therein is generally below 7 and secondly in the methane phase digester in which sulfate reducing bacteria that solubilize metals and form metal sulfides are disposed. Metal solubilization in the anaerobic digestion process reduces the need for adding chelating agents in the subsequent clarifying step of the process of this invention.

$CO_2$ stripping of the methane phase liquid effluent in $CO_2$ stripper 12 increases the pH of the methane phase liquid effluent containing solubilized metals to above about 8.5, causing the solubilized metals to precipitate and be removed in clarifier 14. The solubilized metals may also be precipitated by the addition of caustic or lime to clarifier 14 to provide a pH in the range of about 9 to about 10. In some extreme cases, chelating agents may be added in conjunction with the pH reducing agent. Similarly, depending upon the type of heavy metals and the effluent chemistry, a pH swing of about 2 to about 12 may be required for metal solubilization and subsequent precipitation.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A process for improved methane production by two-phase anaerobic digestion of organic carbonaceous material comprising the steps of:

introducing said organic carbonaceous material into an acid phase digester;

fermenting said organic carbonaceous material in said acid phase digester under anaerobic conditions, forming a liquid/solids effluent;

passing said liquid/solids effluent to a methane phase digester;

fermenting said liquid/solids effluent in said methane phase digester under anaerobic conditions and withdrawing gas comprising methane from said methane phase digester;

passing a methane phase liquid effluent to a $CO_2$ stripper and stripping $CO_2$ and $H_2S$ from said methane phase liquid effluent; and introducing a stripper liquid effluent comprising dissolved oxygen into said methane phase digester.

2. A process in accordance with claim 1, wherein, prior to introduction into said acid phase digester, said organic carbonaceous material is separated into a less biodegradable portion and a first more biodegradable portion, and said less biodegradable portion is introduced into a bioleaching reactor and bioleached, forming a leachate and a second more biodegradable portion.

3. A process in accordance with claim 2, wherein said leachate is introduced into said acid phase digester.

4. A process in accordance with claim 1, wherein said methane phase digester is a non-mechanically mixed reactor.

5. A process in accordance with claim 1, wherein said dissolved oxygen comprises between about 2 mg/l of methane phase digester volume—day to about 50 mg/l of methane phase digester volume—day.

6. A process in accordance with claim 2, wherein a portion of said stripper liquid effluent is clarified, aerated and subsequently introduced into said bioleaching reactor.

7. A process in accordance with claim 6, wherein said aeration of said stripper liquid effluent is sufficient to prevent growth of a methane producing microbial population in said stripper liquid effluent.

8. In a two-phase anaerobic digestion process for improved methane production in which an organic carbonaceous material is fermented in an acid phase digester and a liquid/solids effluent from said acid phase digester is fermented in a methane phase digester forming a gas comprising methane and a liquid effluent, the improvement comprising:

introducing oxygen into a liquid phase of said methane phase digester.

9. A two-phase anaerobic digestion process in accordance with claim 8, wherein the amount of oxygen introduced into said methane phase digester is between about 2 mg/l of methane phase digester volume—day to about 50 mg/l of methane phase digester volume—day.

10. A two-phase anaerobic digestion process in accordance with claim 8 further comprising bioleaching at least a portion of said organic carbonaceous material prior to fermenting in said acid phase digester.

11. A two-phase anaerobic digestion process in accordance with claim 8, wherein said liquid effluent is introduced into a $CO_2$ stripper and dissolved $CO_2$ and $H_2S$ in said liquid effluent are stripped from said liquid effluent.

12. A two-phase anaerobic digestion process in accordance with claim 11, wherein said oxygen is dissolved in a liquid stripper effluent from said $CO_2$ stripper and said liquid stripper effluent is introduced into said methane phase digester.

13. A two-phase anaerobic digestion process in accordance with claim 12, wherein solubilized metals in said liquid stripper effluent are removed therefrom.

* * * * *